(12) United States Patent
Hall et al.

(10) Patent No.: US 10,154,855 B2
(45) Date of Patent: Dec. 18, 2018

(54) SKIN GRAFT DEVICES AND METHODS

(71) Applicant: KCI Licensing, Inc., San Antonio, TX (US)

(72) Inventors: Colin John Hall, Poole (GB); Anissa Lloyd, San Antonio, TX (US); Christopher Brian Locke, Bournemouth (GB); Paul S. Slack, San Jose, CA (US)

(73) Assignee: KCI Licensing, Inc., San Antonio, TX (US)

( * ) Notice: Subject to any disclaimer, the term of this patent is extended or adjusted under 35 U.S.C. 154(b) by 126 days.

(21) Appl. No.: 15/270,978

(22) Filed: Sep. 20, 2016

(65) Prior Publication Data

US 2017/0042561 A1 Feb. 16, 2017

Related U.S. Application Data

(63) Continuation of application No. 13/451,174, filed on Apr. 19, 2012, now Pat. No. 9,468,459.

(60) Provisional application No. 61/477,485, filed on Apr. 20, 2011.

(51) Int. Cl.
    *A61B 17/322* (2006.01)
    *A61B 17/3205* (2006.01)
    *A61B 10/02* (2006.01)
    *A61B 17/00* (2006.01)
    *A61B 17/30* (2006.01)

(52) U.S. Cl.
    CPC ...... *A61B 17/322* (2013.01); *A61B 17/32053* (2013.01); *A61B 10/0233* (2013.01); *A61B 2017/00561* (2013.01); *A61B 2017/00734* (2013.01); *A61B 2017/306* (2013.01)

(58) Field of Classification Search
    CPC .................... A61B 17/322; A61B 17/32053
    See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Guiles, Jr. |
| 3,568,675 A | 3/1971 | Harvey |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.

(Continued)

*Primary Examiner* — Richard Louis

(57) ABSTRACT

Devices and methods for obtaining a plurality of skin tissue particles for use in skin grafting.

7 Claims, 18 Drawing Sheets

(56) References Cited

U.S. PATENT DOCUMENTS

| | | | |
|---|---|---|---|
| 3,628,524 A * | 12/1971 | Jamshidi | A61B 10/025 600/567 |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carlon | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0107527 A1 * | 8/2002 | Burres | A45D 29/14 606/131 |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0055414 A1 * | 3/2003 | Altshuler | A61B 18/203 606/9 |
| 2005/0028828 A1 * | 2/2005 | Heaton | A61F 13/023 128/897 |
| 2006/0259102 A1 * | 11/2006 | Slatkine | A61B 17/205 607/88 |
| 2011/0257588 A1 * | 10/2011 | Knowlton | A61B 17/322 604/22 |
| 2012/0035618 A1 * | 2/2012 | Sabir | A61B 17/322 606/132 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

(56) References Cited

OTHER PUBLICATIONS

S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., MD., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinoví?, V. ?uki?, Ž. Maksimoví?, ?. Radak, and P. Peška, "Vacuum Therapy in the Treatment of Peripheral Blood Vessels," Timok Medical Journal 11 (1986), pp. 161-164 (and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

* cited by examiner

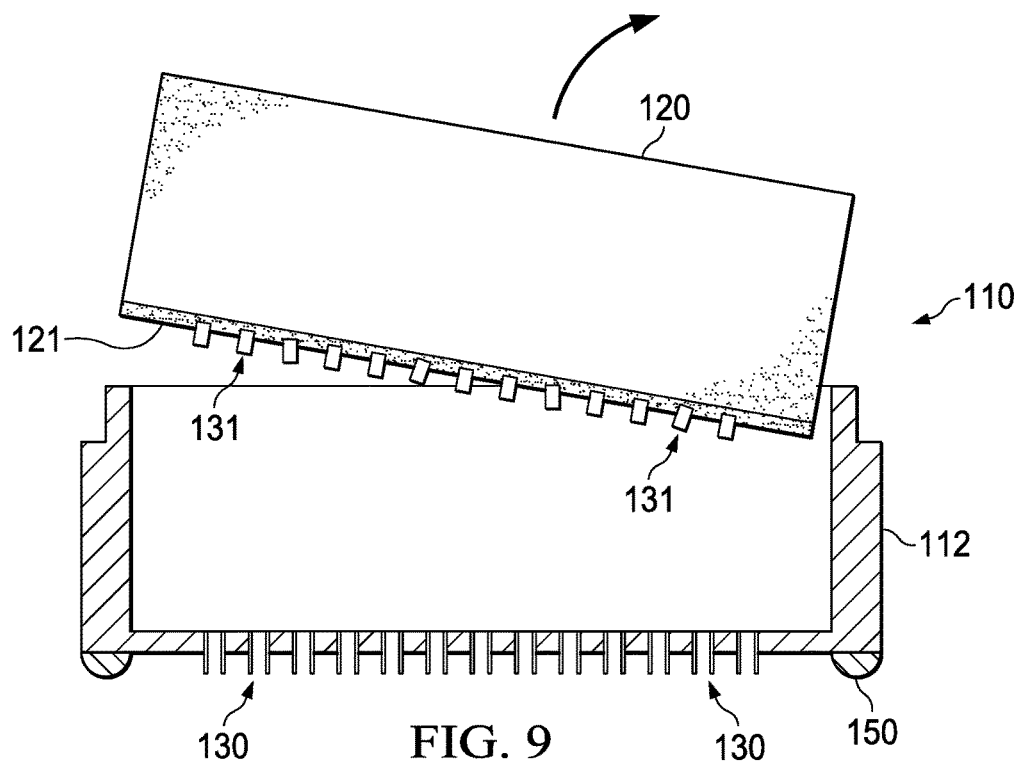
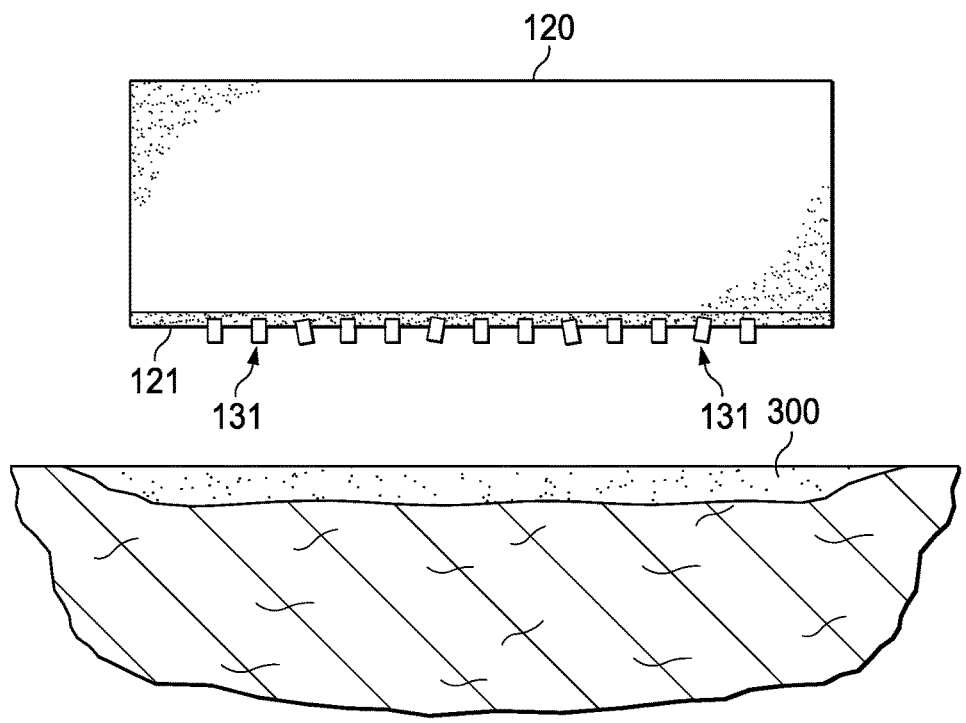
FIG. 10

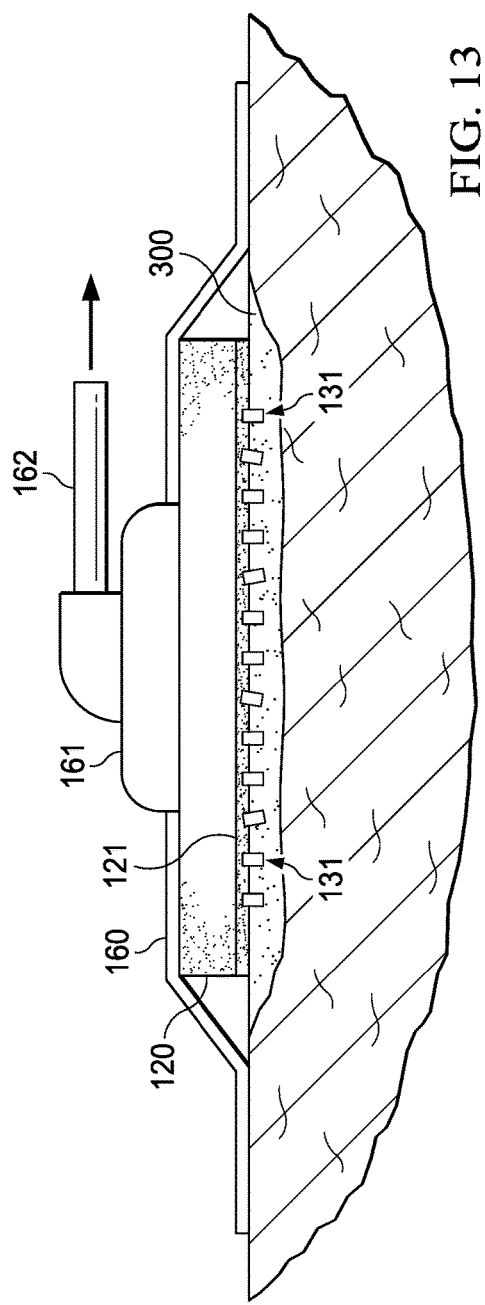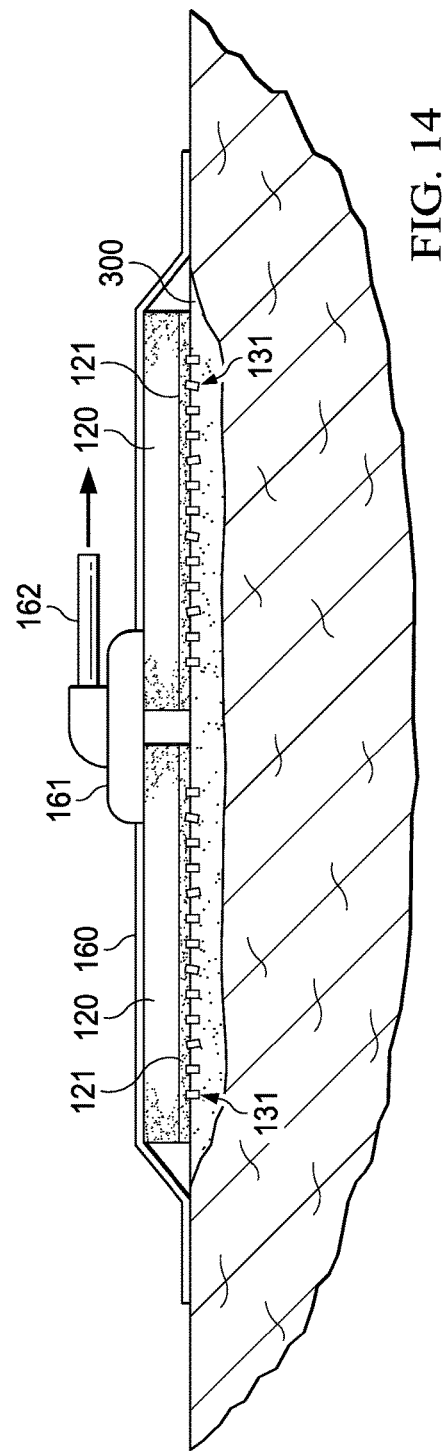

DIAGRAM SHOWS A SECTION THROUGH ONE OF THE NANO-PUNCHES POSITIONED ON DONOR SITE

SKIN GRAFT DEVICES AND METHODS

RELATED APPLICATIONS

This application is a continuation of U.S. patent application Ser. No. 13/451,174, filed Apr. 19, 2012, which claims the benefit under 35 USC 119(e), of the filing of U.S. Provisional Patent Application No. 61/477,485, entitled "Skin Graft Devices and Methods," filed Apr. 20, 2011, the entire contents of which are incorporated herein by reference.

BACKGROUND

1. Field of the Invention

The present invention relates generally to skin grafting and related devices and methods. The present invention provides a systematic approach to the process of skin grafting, i.e., harvesting, post-excision processing and application of donor skin and treatment of the graft recipient site.

2. Background Information

Advances in medical technology have provided many patients with benefits inconceivable a century ago. In particular, skin grafting has enabled doctors to heal wounds with the patient's own skin from a harvest site on the patient. The skin grafting techniques have many wonderful benefits, but are still replete with a number of problems.

The process of split-thickness skin grafting can be envisaged as a series of steps; (1) harvesting the split-thickness-skin graft ("STSG") at a donor site; (2) processing of excised STSG; (3) application of the processed skin to the wound site; and (4) pre- and/or post-graft treatment to accelerate healing of the wound site. Each of these steps interposes various challenges and obstacles, e.g., technical, therapeutic and financial, in executing a successful graft.

In regard to the first step, harvesting a STSG at a donor site has traditionally been accomplished using powered, hand-held dermatomes. These devices are expensive and the operation is known to be highly dependent on user skill and training, and requires involved procedures to accurately obtain a successful harvest. These devices must be operated at a precise constant angle relative to the skin, with the exact amount of pressure to insure a uniform harvest. Slight variations in operative use of these dermatomes result in excised skin of variable-thickness, which sometimes must be discarded altogether. As a result, these devices are primarily wielded only by experienced plastic surgeons. Use of these dermatomes are generally confided to the operating room setting, increasing the cost of the procedure, especially given the average fee for operating room use.

There is a current need for harvesting procedures that require a lower degree of operator skill and are capable of being performed outside of an operating room, thus decreasing the costs of the procedure.

In regard to the second step of processing excised skin, it is highly desirable to maximize the coverage of the donor skin at the wound site for any given area of a potential donor site. Apart from minimizing trauma incurred at the donor site, a major factor limiting survival following extensive injury is insufficient availability of donor sites to provide enough skin for the required grafting procedures. One procedure is to mesh the skin graft i.e., creating slits in the excised donor skin to allow for the skin to be stretched. A graft-meshing machine is commonly used in hospital-based surgical practices, and generally allow for an expansion ratio of 3:1 to 9:1. The excised harvested skin is placed on a specific template, depending on the expansion ratio desired, and the template and graft are pressed through the mesher. While greater ratios than 9:1 may be possible using meshing techniques, there is a concomitant significant delay in epithelialization with using such ratios. When healed, a meshed grafted site characteristically has a permanent "crocodile skin" or "weaved" appearance.

Micro grafting techniques, in which the donor tissue is actually minced in order to achieve a greater than 10:1 expansion ratio, are known in the art. Such techniques allow for a greater coverage area from a small donor site than meshing techniques. Traditional micrograft techniques, dating back to 1963, utilized minced skin that is between ⅛th inch (approximately 3 mm, or 3000 µm) and 1/16th inch (approximately 1.5 mm, or 1500 µm) in size. However, disadvantages of using pieces larger than 1500 µm have been noted. For example, in skin pieces of this size cells remote from a cut edge have a limited availability to migrate and proliferate and thereby contribute to forming new skin. In addition, the techniques employed have required each piece to be oriented epidermis upwards, making the procedure tedious and impractical. Further, the appearance of the new skin that is produced using particles of this size is poor, often having a cobblestone appearance.

There is currently a need for a procedure capable of producing micrograft particles in a size less than 1500 µm in a rapid and efficient manner, with a minimum of handling procedures, while resulting in skin pieces that are viable and capable of "taking" when applied to a wound site. Such technique would significantly aid in the ease and speed of operations utilizing micrografts.

The third step of the graft procedure, application of processed excised skin to the wound site, it is particularly relevant to the application of micrograft particles to a wound site. Current methods of distributing micrografts, such as mechanical spreading results in clumps or aggregates of skin particles, frustrating an even distribution. In addition, in larger aggregates, some micrograft particles will not be in direct contact with the wound bed. Such particles cannot readily integrate with the wound bed and also will have a reduced potential for nourishment from the wound fluid exudates and consequently have a decreased potential to remain viable. Thus, the aggregation of micrografts reduces the efficiency of epithelialization and may significantly increase the time required to close a wound.

There is a current need for devices and methods to effect an even distribution of micrcograft particles on a wound surface, thereby promoting the efficiency of epithelialization.

The fourth step of the graft procedure relates to pre- and/or post-graft treatment to accelerate healing of the wound site. As is known in the art, closure of surface wounds involves the inward migration of epithelial, dermal and subcutaneous tissue adjacent to the wound. This migration is ordinarily assisted through the inflammatory process, whereby blood flow is increased and various functional cell types are activated. Through the inflammatory process, blood flow through damaged or broken vessels is stopped by capillary level occlusion; thereafter, cleanup and rebuilding operations may begin.

SUMMARY

Certain embodiments of the present disclosure comprise devices and methods relating generally to skin grafting. Particular embodiments provide a systematic approach to the process of skin grafting, i.e., harvesting, post-excision processing and application of donor skin and treatment of the graft recipient site.

Certain embodiments of the present disclosure comprise a device for obtaining a plurality of skin tissue particles for use in skin grafting. In particular embodiments, the device includes a dressing comprising a first surface configured to retain a plurality of skin tissue particles; a housing configured to receive the dressing, wherein the housing comprises a first aperture configured to be coupled to a vacuum source; and a plurality of hollow needles proximal to the first surface of the dressing. In certain embodiments, the first surface comprises a gel. In specific embodiments, the gel is a polyurethane film, an extra-cellular matrix (e.g. collagen), or a silicone based polymer.

In particular embodiments, the plurality of hollow needles are tapered. In specific embodiments, the plurality of hollow needles are tapered such that each of the plurality of needles comprises a larger end proximal to the first surface of the dressing. In certain embodiments, the housing comprises a seal configured to extend around the plurality of hollow needles. In particular embodiments, during use, the plurality of hollow needles are placed proximal to a donor site contained within the seal.

In specific embodiments, the dressing is located between the plurality of hollow needles and the first aperture. In particular embodiments, the dressing is removable from the housing, and in certain embodiments, the housing comprises a first aperture configured to be coupled to a bellows.

Exemplary embodiments also comprise a method of obtaining a plurality of skin tissue particles for use in skin grafting, the method comprising: placing a first device according to claim 1 onto a first donor site; applying negative pressure to the first device; removing a first plurality of skin tissue particles from the first donor site; removing a first dressing from the housing of the first device, wherein the first plurality of skin tissue particles are retained on the first surface of the dressing; and placing the first dressing on a graft site, where the first plurality of skin tissue particles are proximal to the graft site.

Particular embodiments may also comprise covering the dressing and the graft site with a drape; and applying negative pressure to a region under the drape. Certain embodiments may further comprise: placing a second device onto the donor site and applying negative pressure to the second device; removing a second plurality of skin tissue particles from the donor site; removing the second dressing from the housing of the second device, wherein the second plurality of skin tissue particles are retained on the first surface of the second dressing; and placing the second dressing on the graft site, wherein the second plurality of skin tissue particles are proximal to the graft site.

Certain embodiments may also comprise a device for obtaining a plurality of skin tissue particles for use in skin grafting, the device comprising: a processor configured to process skin tissue into a plurality of skin tissue particles; and a container configured to retain the plurality of skin tissue particles, wherein the processor comprises a first cutting surface configured to penetrate skin tissue at a donor site and a second cutting surface that rotates.

In particular embodiments, the first surface comprises a punch configured to penetrate skin tissue and the second cutting surface is configured to sever skin tissue from the donor site. In certain embodiments, the second cutting surface rotates in a plane generally parallel to the skin tissue of the donor site. In specific embodiments, the second cutting surface rotates in a plane generally perpendicular to the skin tissue. In particular embodiments, the processor is manually operated. In certain embodiments, the processor is electrically powered. In specific embodiments, the device is configured such that the device can be separated from the processor.

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

BRIEF DESCRIPTION OF THE DRAWINGS

FIGS. 6-14 illustrate section views of the embodiment of FIGS. 1-5 during use.

DESCRIPTION OF ILLUSTRATIVE EMBODIMENTS

Figure 1:
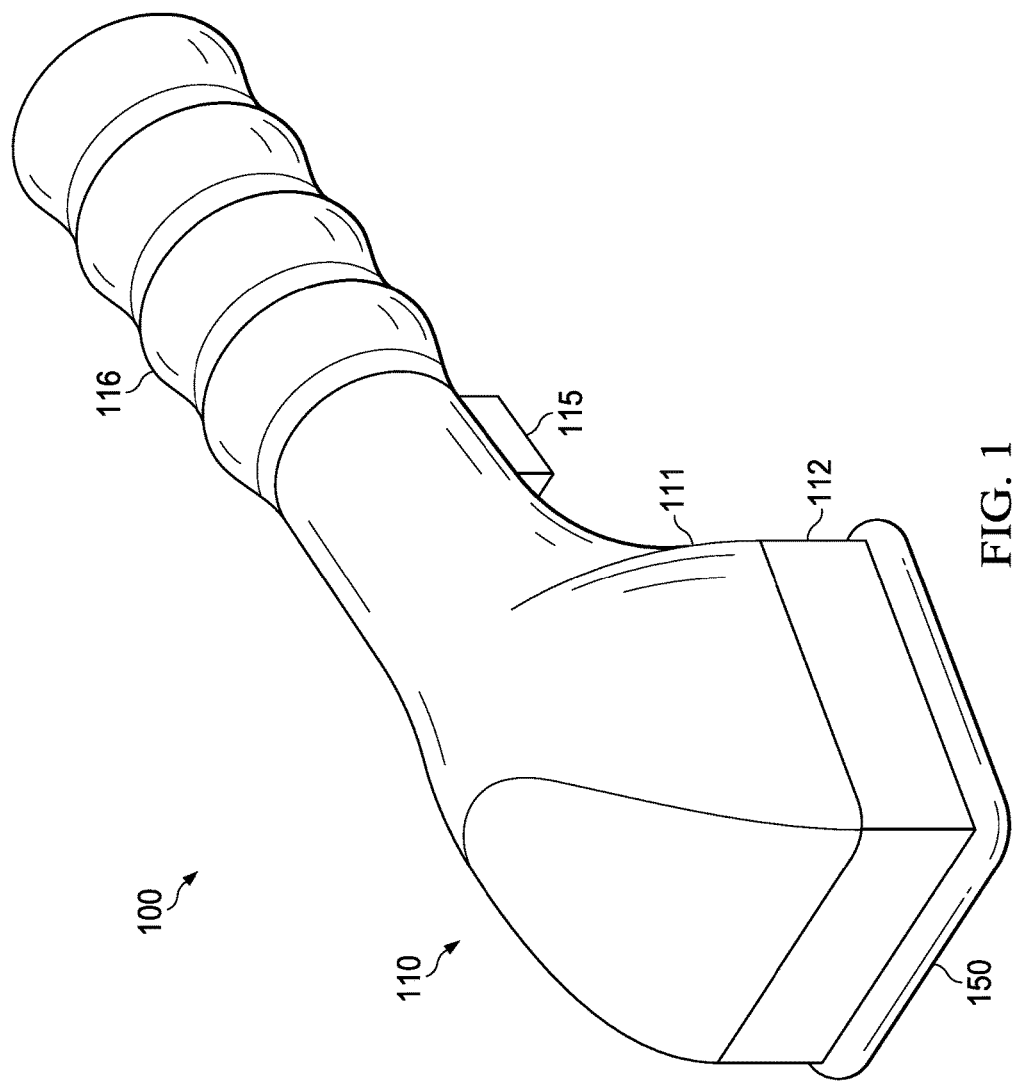
FIGS. 1-5 illustrate perspective and section views of a first exemplary embodiment.
Figure 2:
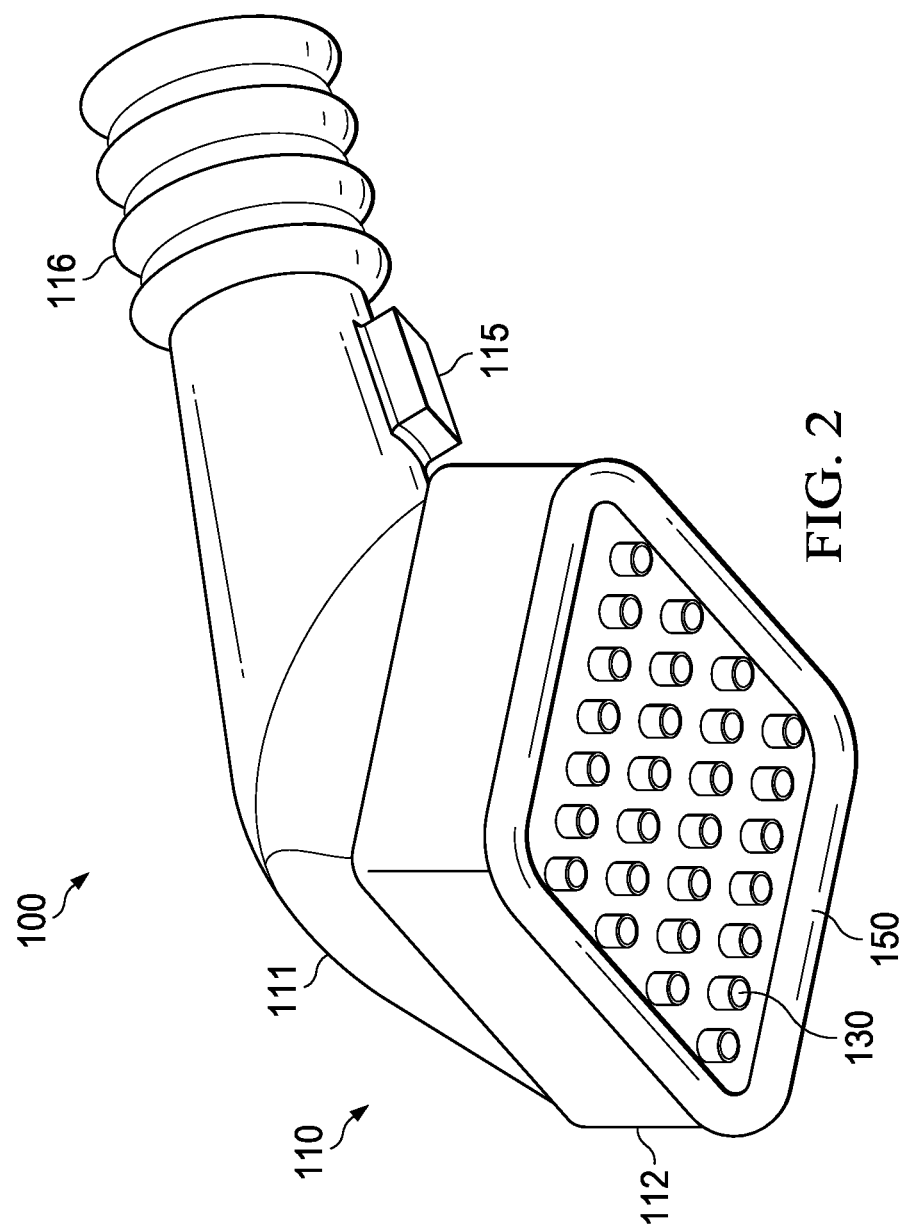
Figure 3:
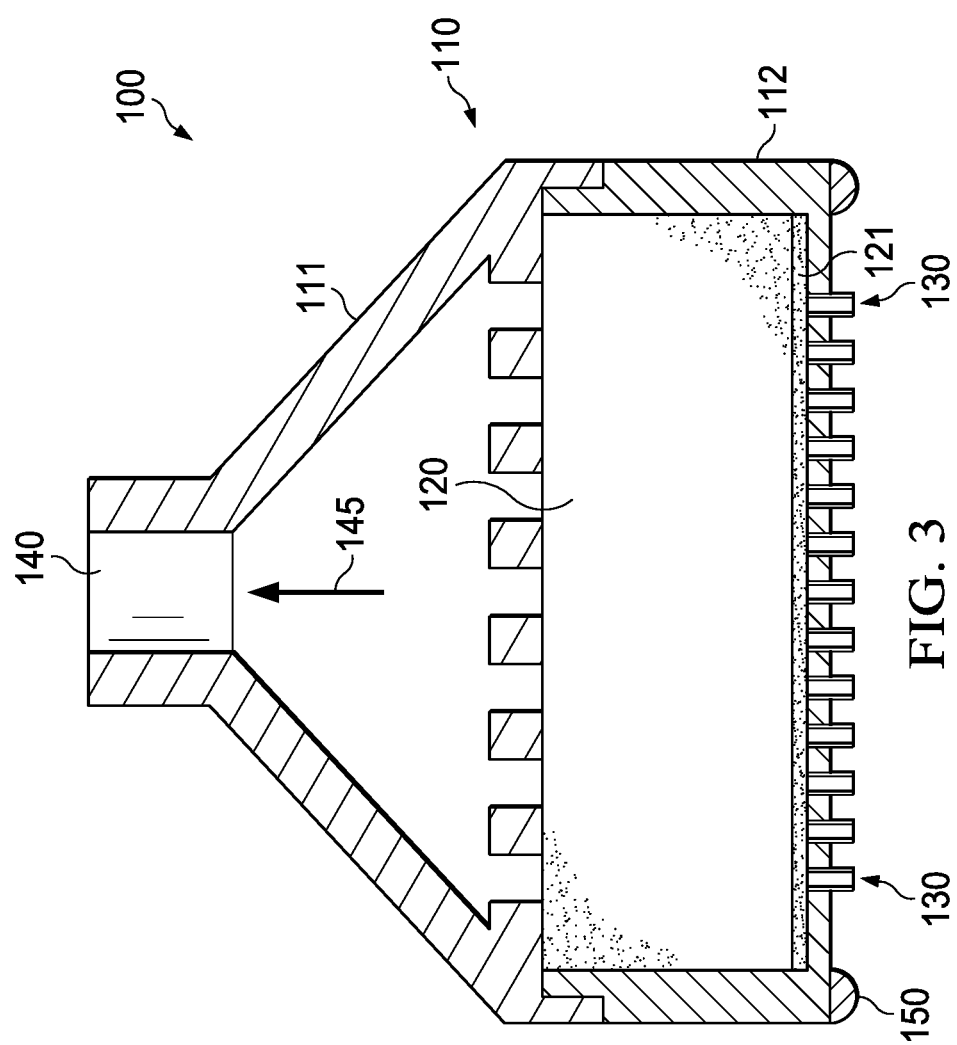

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a wound-treatment method that "comprises," "has," "includes" or "contains" one or more steps possesses those one or more steps, but is not limited to possessing only those one or more steps. Likewise, a wound dressing that "comprises," "has," "includes" or "contains" one or more elements possesses those one or more elements, but is not limited to possessing only those elements.

Further, a device or structure that is configured in a certain way is configured in at least that way, but it can also be configured in other ways than those specifically described.

Referring now to FIGS. 1-5, a device 100 for obtaining skin tissue particles for use in skin grafting is shown. Device 100 comprises a housing 110 that is configured to receive a dressing 120. In certain embodiments, housing 110 may comprise a first portion 111 and a second portion 112 that may be coupled together or separated to allow the contents within housing 110 to be removed. In the embodiment shown, device 100 also comprises a plurality of hollow needles 130, which are configured to penetrate tissue during use and remove skin particles from a harvest site. In the illustrated embodiment, device 100 further comprises a seal 150 configured to seal an area around the plurality of needles 130.

An overview of the operation of device 100 will be provided initially, followed by a more detailed description. During operation, device 100 can be placed on a skin harvest site such that hollow needles 130 are in contact with the harvest site and seal 150 has sealed the area within the harvest site. A low pressure source 116 (e.g. a bellows device, a vacuum pump or other suitable device) can be coupled to aperture 140 and operated to provide a low pressure region within housing 110. In the embodiment shown, a switch 115 can control operation of low pressure source 116.

The operation of low pressure source 116 can cause air to flow in the direction of arrow 145 (see FIG. 3) and draw the harvest site toward needles 130. Skin tissue from the harvest site can be drawn into needles 130 and removed from the harvest site. In certain embodiments, device 100 may be vibrated or laterally translated to assist in the removal skin tissue from the harvest site. In particular embodiments, hollow needles 130 may be tapered as shown in the cross-section view of FIG. 5 such that an end 131 proximal to dressing 120 is larger than an end 132 distal from dressing 120.

Figure 4:
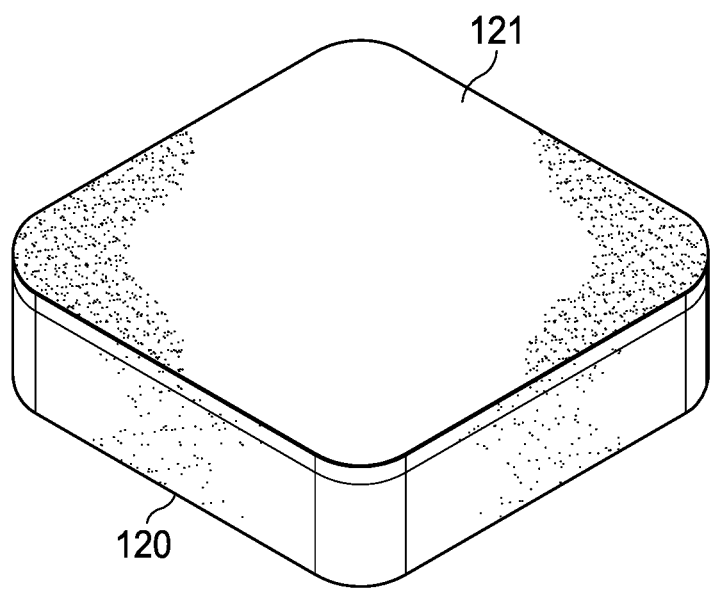
Figure 5:
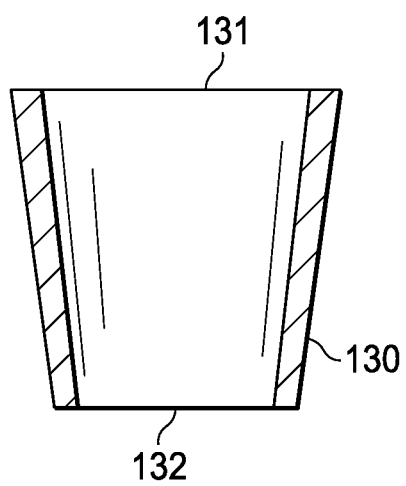

When the skin tissue is removed from the harvest site, the tissue particles contact dressing 120, which includes a surface 121 that is configured to retain the particles when dressing 120 is removed from housing 110. A perspective view of dressing 120 removed from housing 110 is shown in FIG. 4. Dressing 120 can then be placed on a graft site oriented such that surface 121 and the tissue particles are in contact with the graft site. In certain embodiments, a negative pressure wound therapy can then be applied to the graft site to assist in the grafting of the tissue particles to the graft site.

Figure 6:
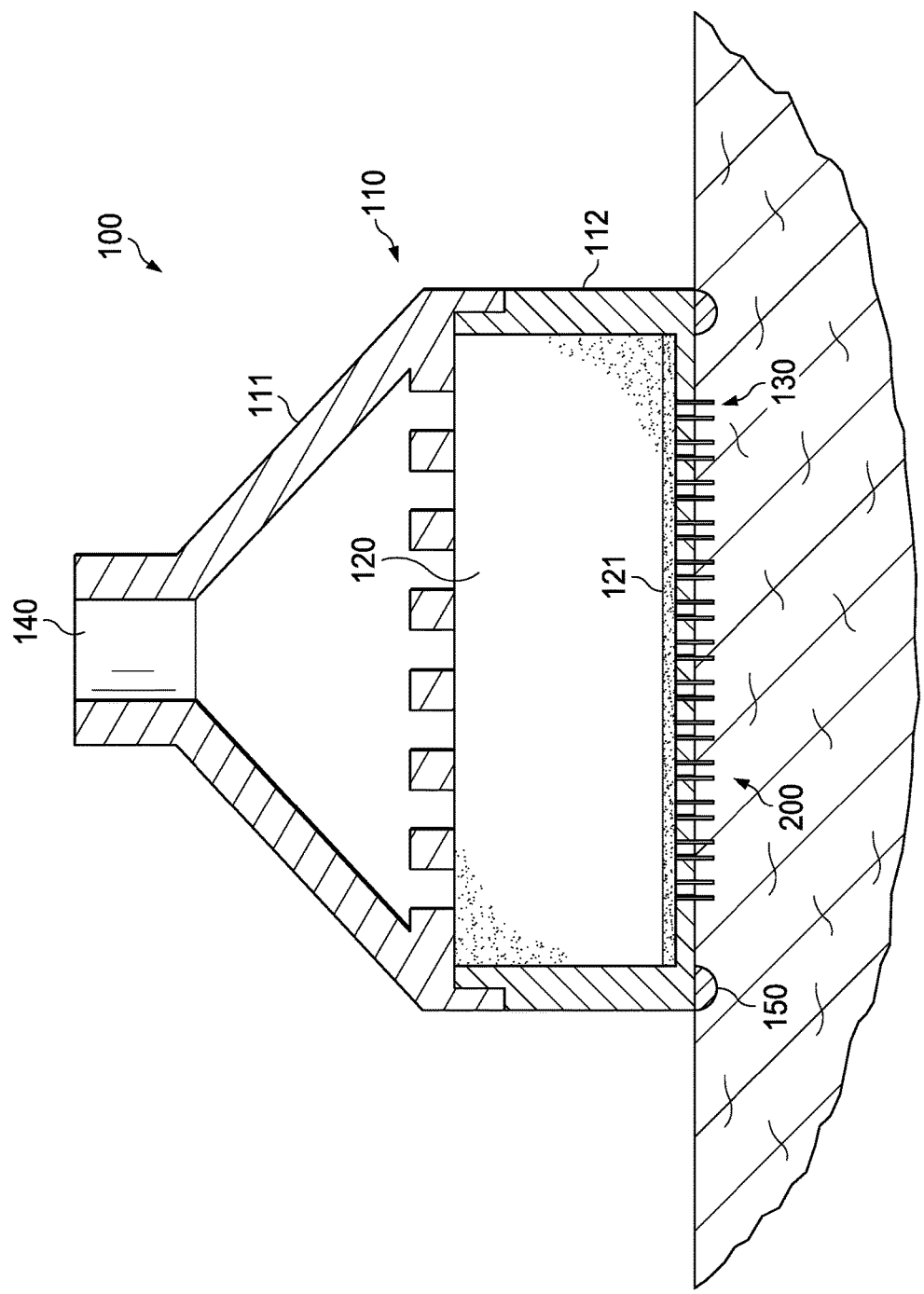
Figure 7:
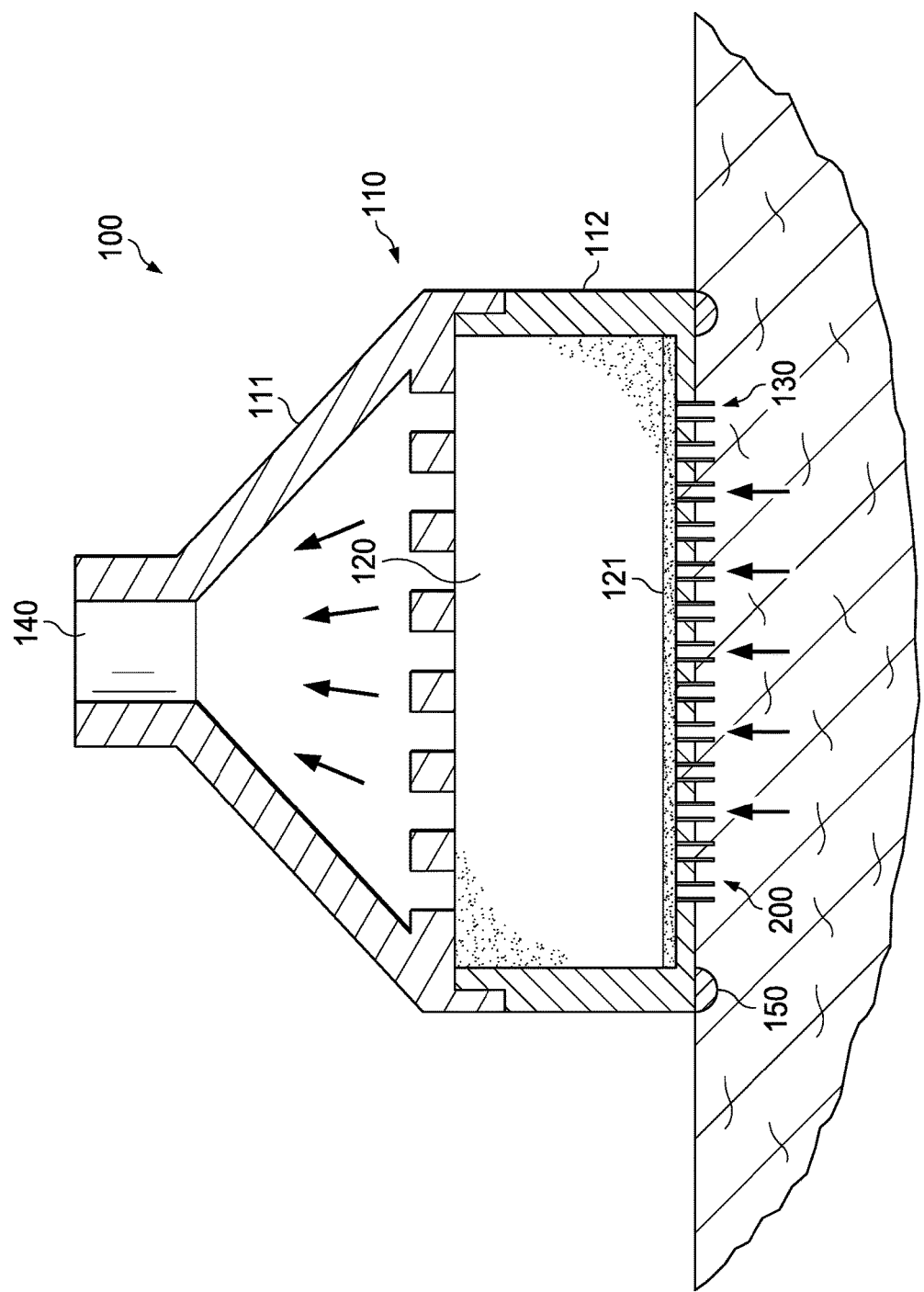

Referring now to FIGS. 6-13, a description of individual steps in an exemplary method of use will be provided. As shown in FIG. 6, device 100 has been placed on a donor site 200 such that needles 130 are in contact with the skin tissue at donor site 200 and seal 150 has sealed the area of donor site around needles 130. Referring now to FIG. 7, a negative pressure source (in fluid communication with device 100 via aperture 140) has been operated to provide a negative pressure to device 100. With negative pressure applied, tissue from donor site 200 is drawn into needles 130 to a controlled depth so that the tissue extends through needles 130 and to surface 121 of dressing 120. Device 100 can then be manipulated (e.g. vibrated, laterally translated, or other suitable action) to remove skin tissue particles 131 from donor site 200. When device 100 is removed from donor site 200, skin tissue particles 131 are retained by surface 121 of dressing 120. In particular embodiments, surface 121 may comprise a gel configured to retain the skin tissue particles by adhering the particles to the layer.

Figure 8:
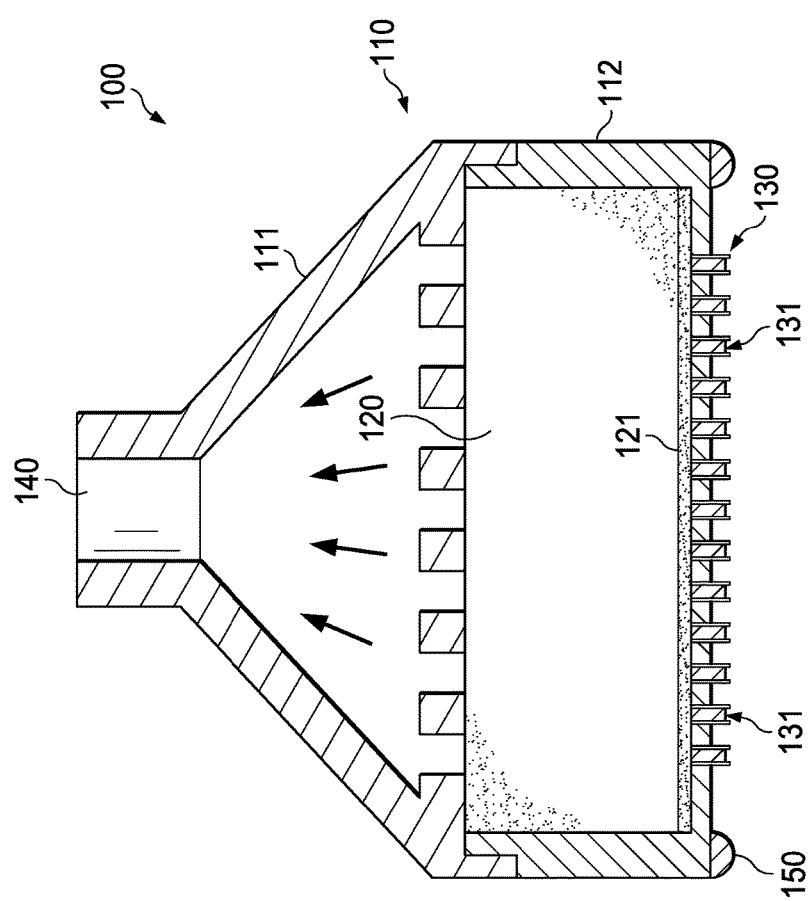

As shown in FIG. 8, device 100 has been removed from donor site 200 and surface 121 has retained skin tissue particles 131 after removal from donor site 200. Referring now to FIG. 9, first portion 111 of device 100 has been separated from second portion 112. This can allow dressing 120 to be removed from housing 110 of device 100. As shown in this embodiment, surface 121 continues to retain skin tissue particles 131 with dressing 120 removed from housing 110.

Figure 11:
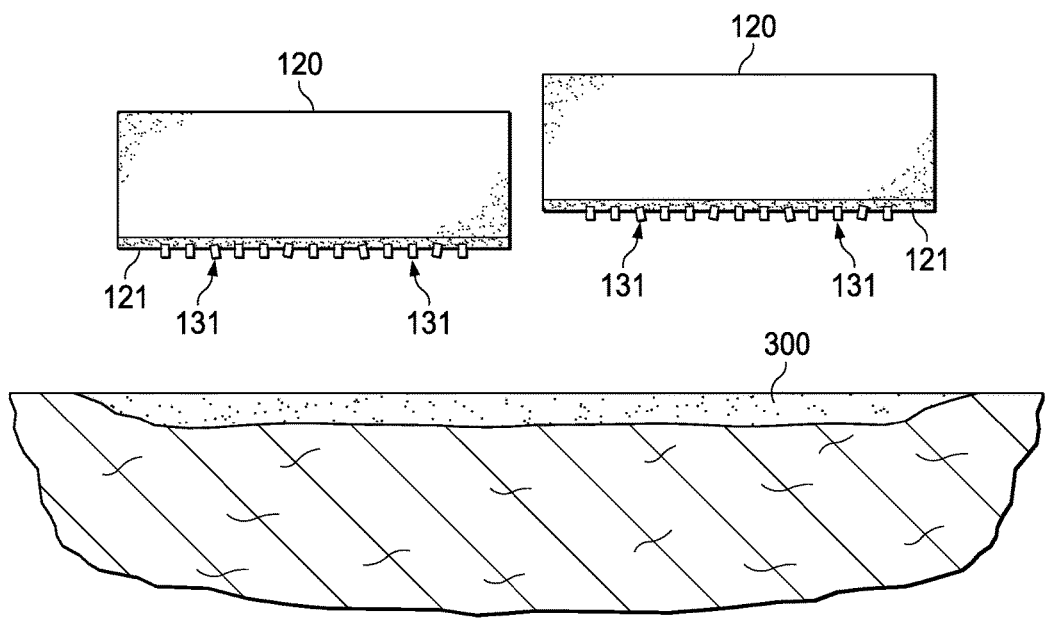

Referring now to FIG. 10, dressing 120 is positioned proximal to a graft site 300 so that skin tissue particles 131 are oriented proximal to graft site 300. As shown in FIG. 11, in certain embodiments, multiple dressings 120 may be placed adjacent to each other in cases where graft site 300 is larger than dressing 120. In specific embodiments, dressing 120 may be configured so that multiple dressings can be placed adjacent to each other to substantially cover graft site 300. For example, in certain embodiments, dressing 120 and surface 121 may be triangular, square, rectangular, hexagonal or other suitable configurations (when viewed from above looking down toward dressing 120 and graft site 300).

Figure 12:
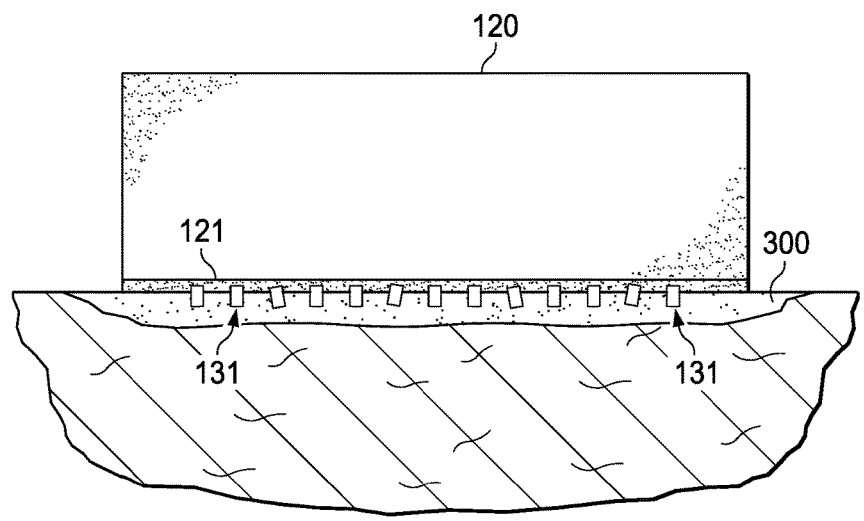
Figure 15:
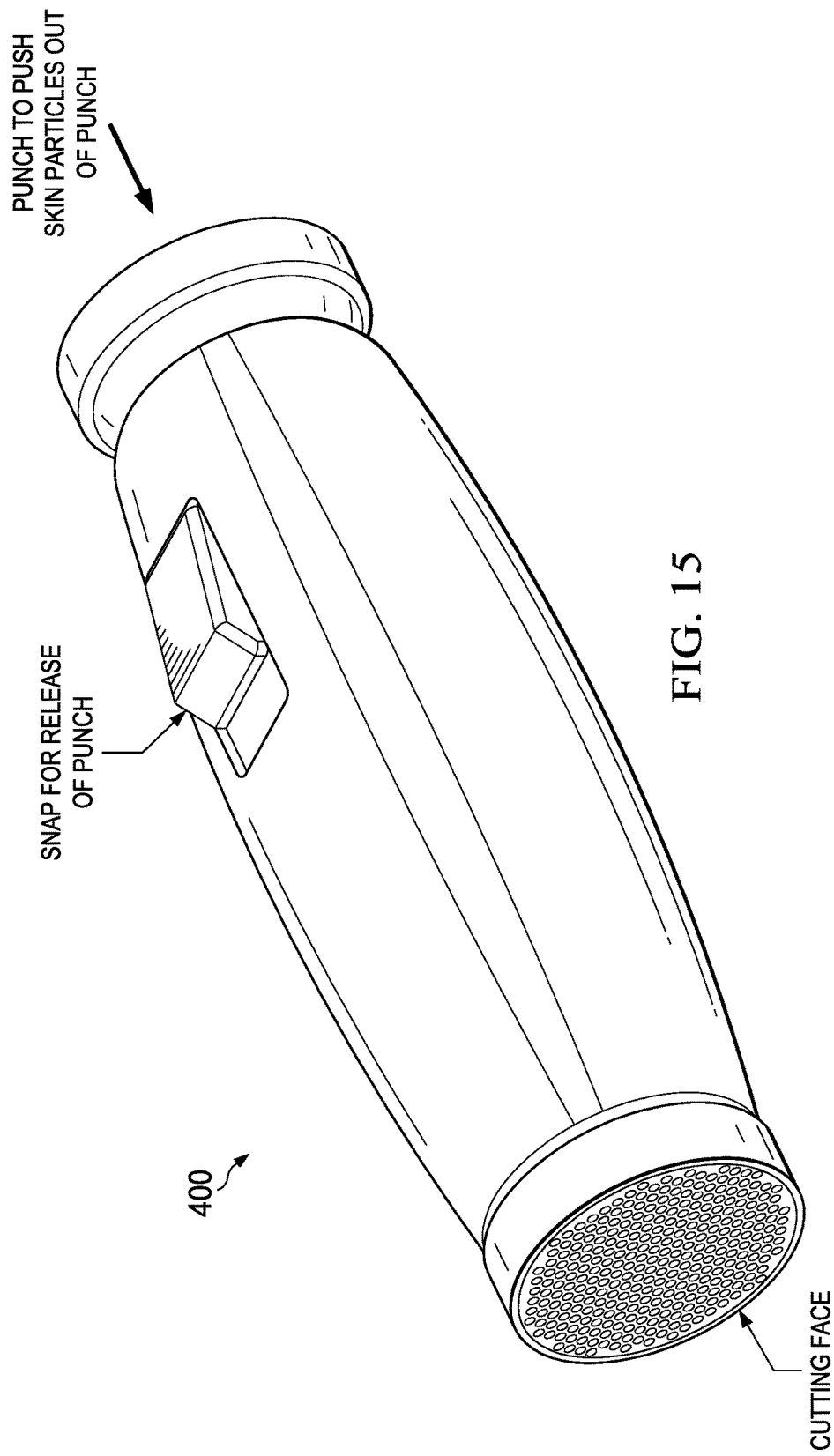
FIGS. 15-18 illustrate perspective and orthographic views of a second exemplary embodiment.
Figure 16:
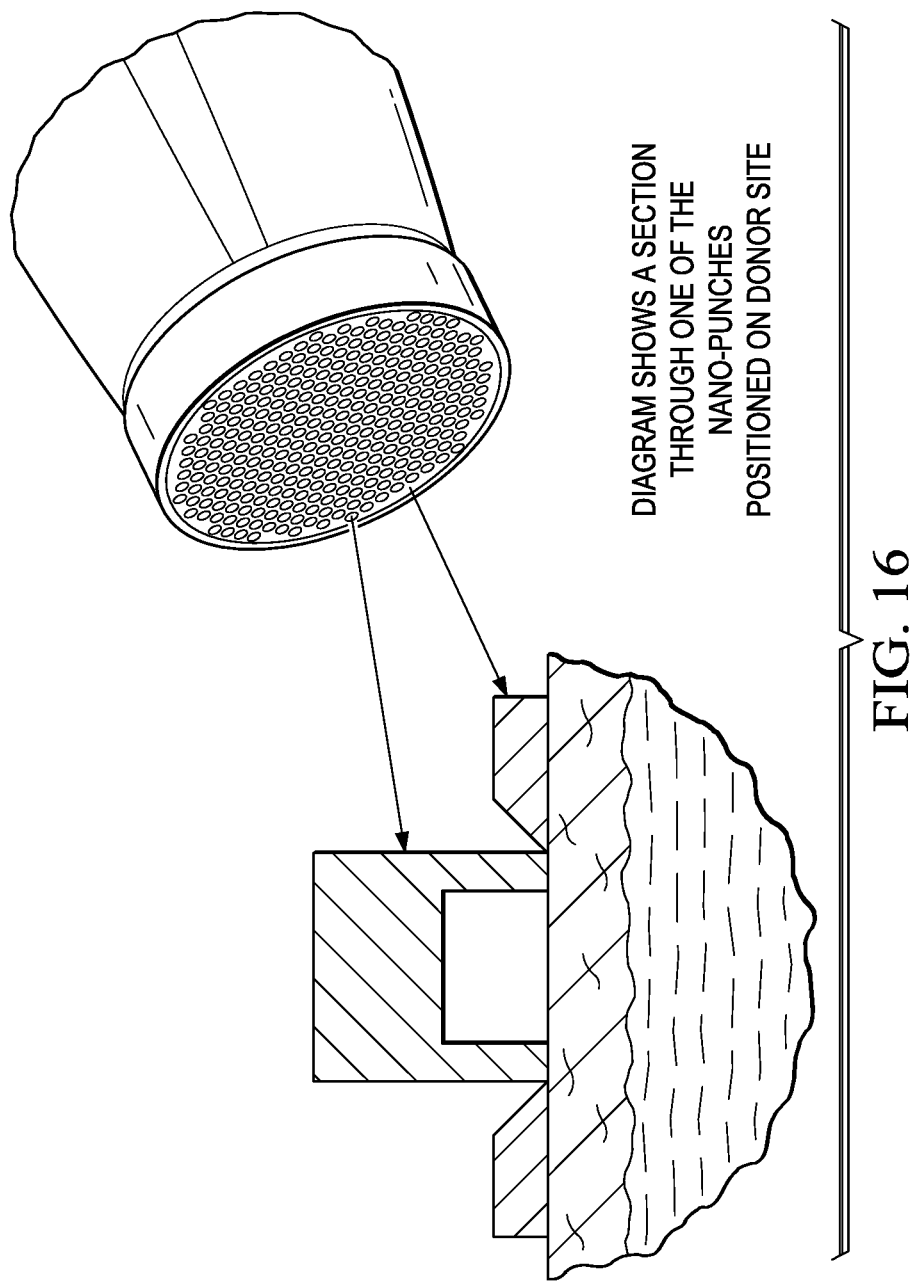
Figure 17:
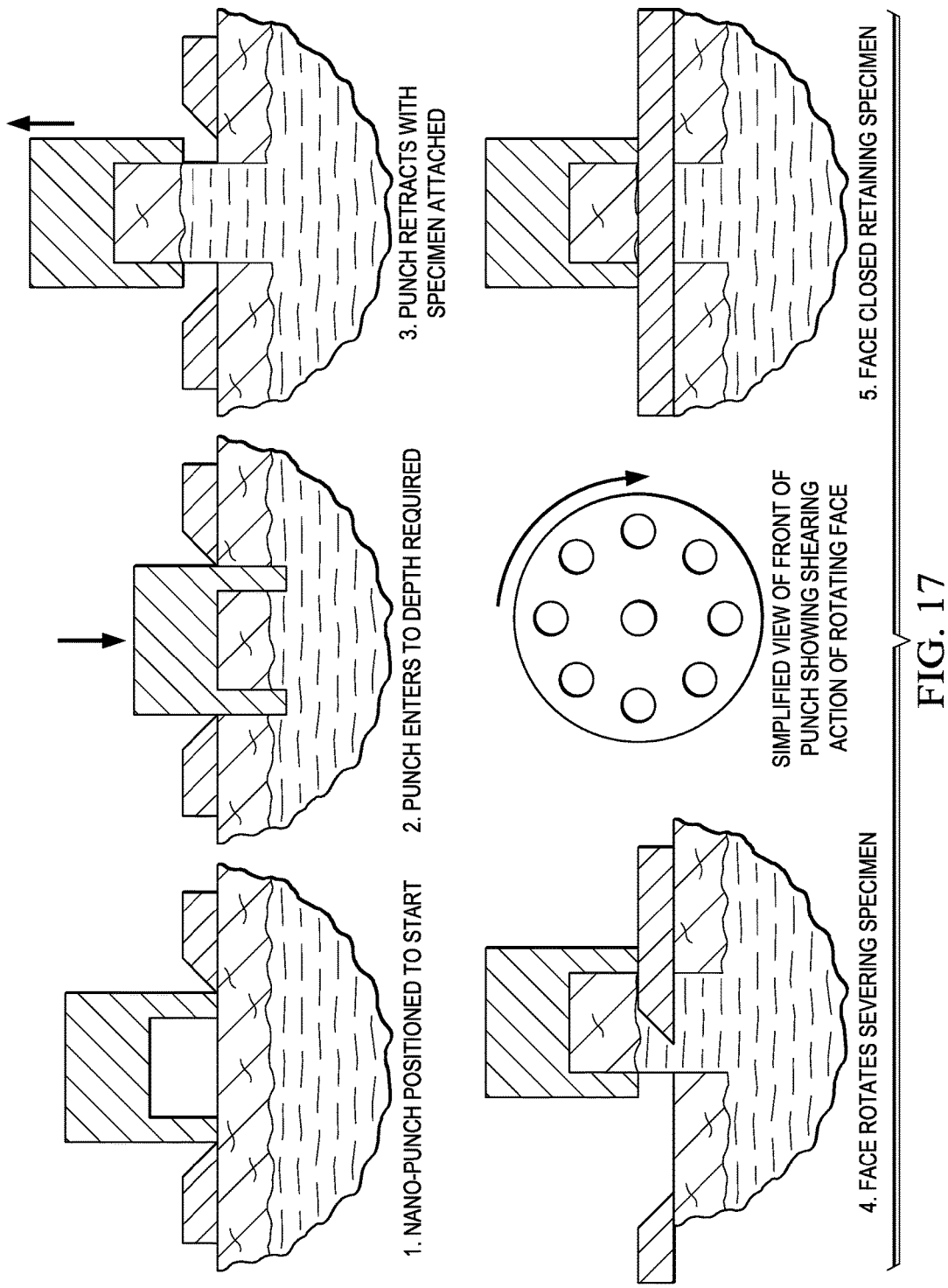
Figure 18:
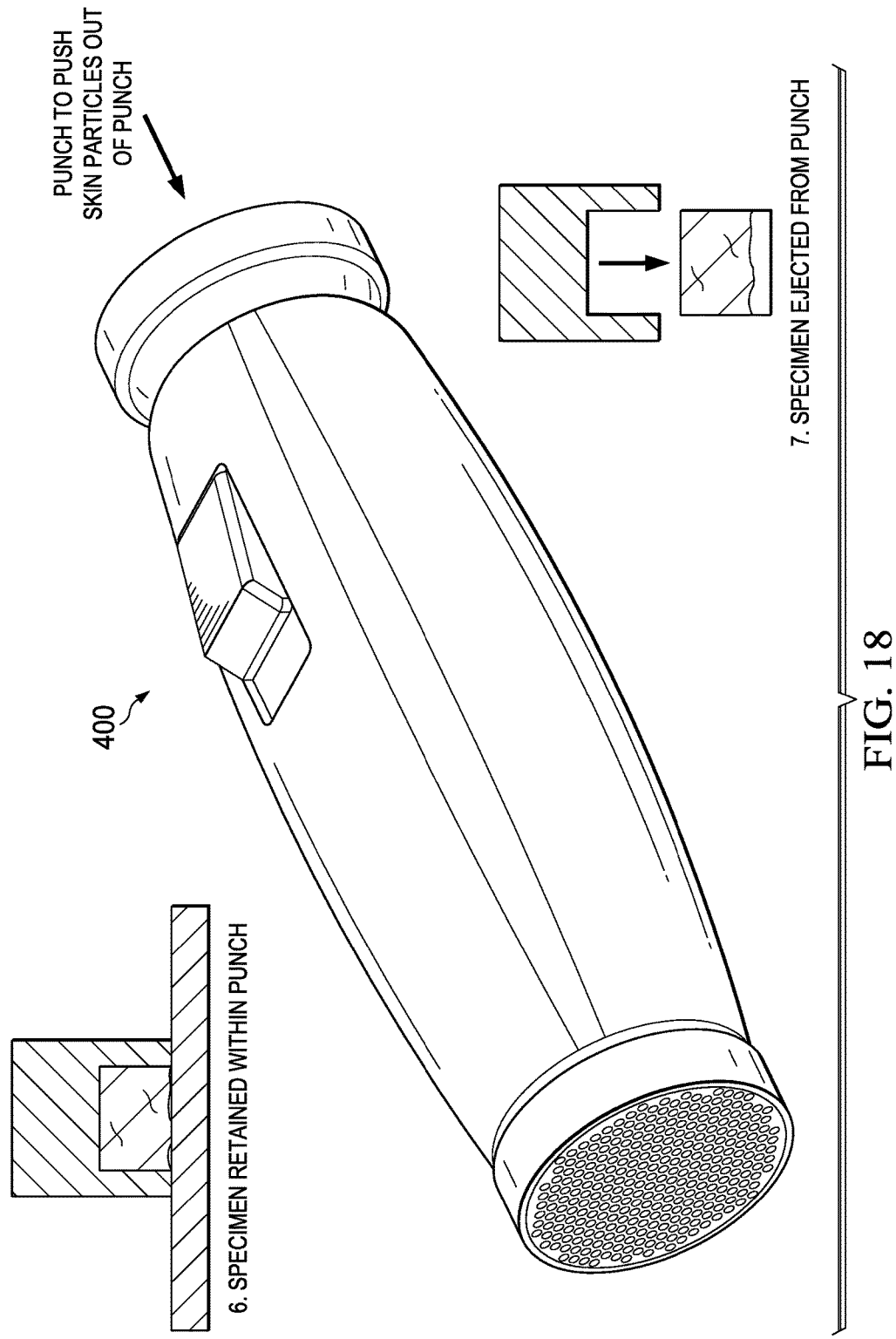

As shown in FIG. 12, dressing 120 is placed on graft site 300 so that skin particles 131 are in contact with graft site 300. As illustrated in FIGS. 8-12, skin tissue particles 131 are retained by surface 121 from the time the particles are harvested from donor site 200 until they are placed on graft site 300. The ability to retain skin tissue particles 131 during the harvesting and grafting process provides many benefits, including the ability to provide a consistent and repeatable delivery of the particles to the graft site. This can increase the likelihood of obtaining a successful graft and improve the uniformity of the graft appearance.

In certain embodiments, negative pressure wound therapy can also be applied to graft site 300. As shown in FIG. 13, a drape 160 has been applied over dressing 120 and graft site 300. In the embodiment shown a coupling member 161 couples a conduit 162 to drape 160 and allows a negative pressure to be applied to the region under drape 160 (including e.g., dressing 120 and graft site 300). As shown in FIG. 14, a larger drape 160 may be used in cases where multiple dressings 120 are needed to cover graft site 300.

Referring now to FIG. 15-18, an exemplary embodiment comprises a unitary dermatome and mincer single use multi-bladed micro punch 400 with a plurality of nano-punches configured to incise the epidermis to the required depth and dimension. The punch can be activated using the snap switch situated on the side of the device. In this embodiment, a disposable tip also incorporates a specimen tray or container, where the processed skin particles are collected. Harvested material is released from the device by pressing the knob on the rear of the device. This embodiment provides a manual operation multi-specimen micro punch device with disposable tip and specimen tray/container. This device is able to harvest the skin particles (or islets) and process them to a ready to use state using simple operations. Additional details regarding the features and operation of the embodiment of FIG. 15-18 can be found in the figures and accompanying description in FIGS. 15-18.

Figure 19:
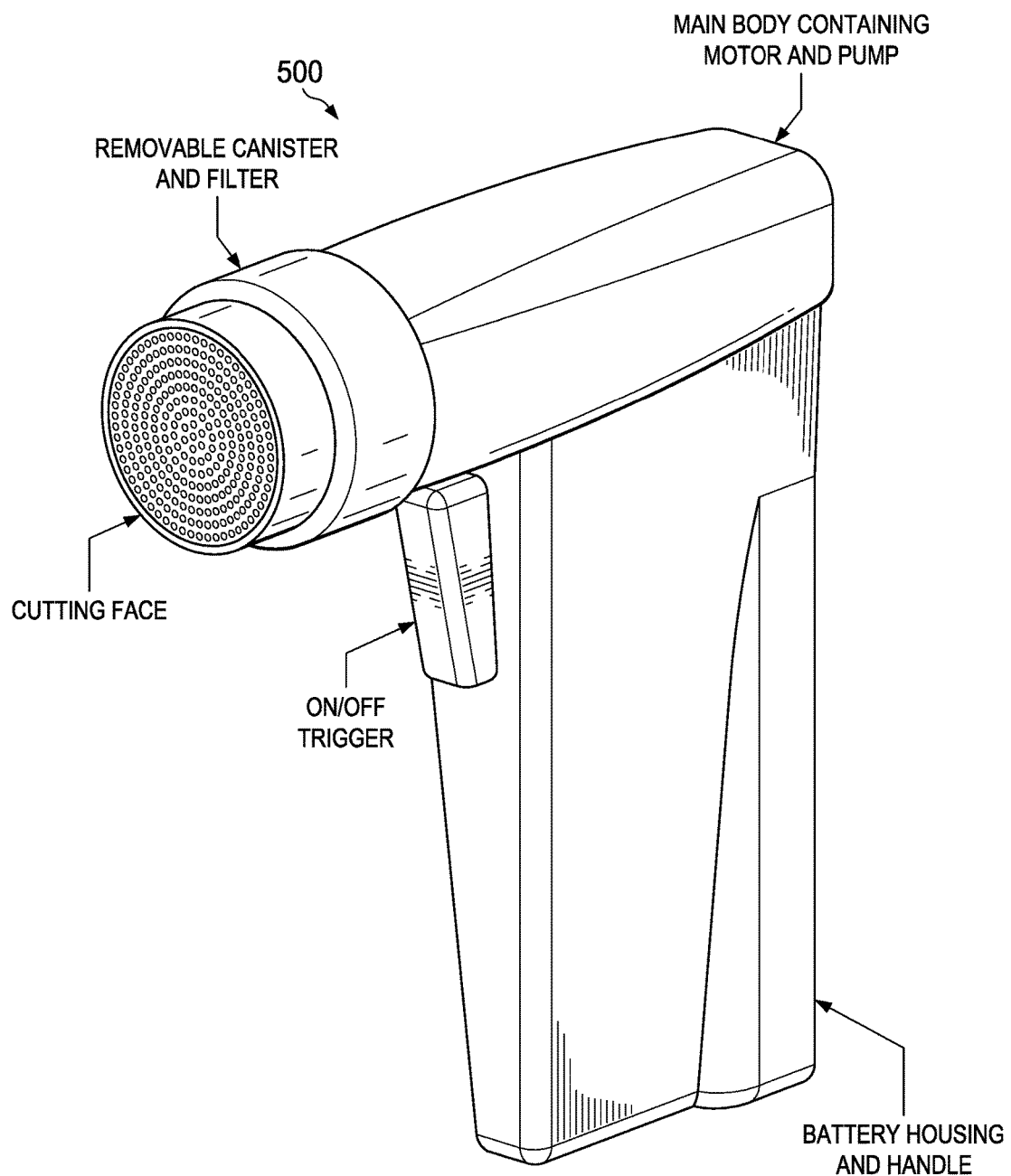
FIGS. 19-20 illustrate perspective and orthographic views of a third exemplary embodiment.
Figure 20:
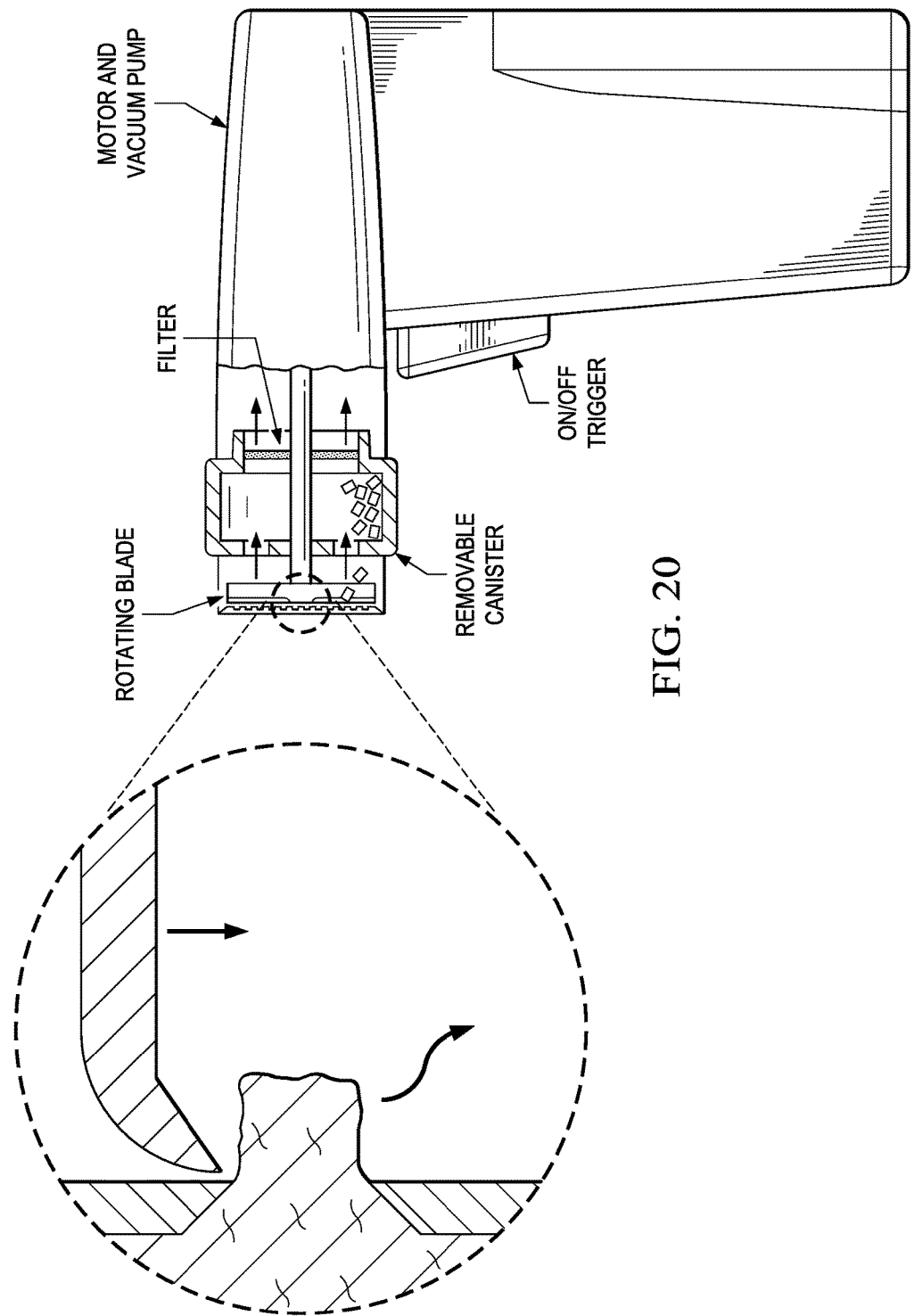

Referring now to FIGS. 19-20, a unitary, battery powered, re-useable dermatome and mincer is shown. In this embodiment, the battery-powered device is placed on the donor site with moderate pressure and activated using the on/off trigger. During operation of this embodiment, the skin tissue can be excised and transferred by vacuum to a removable/disposable collection canister or container. In this exemplary embodiment, the cutting head may also be a disposable component. The canister/container of this device provide easy access to fully processed skin particles. Additional details regarding the features and operation of the embodiment of FIG. 19-20 can be found in the figures and accompanying description in FIGS. 19-20.

Figure 21:
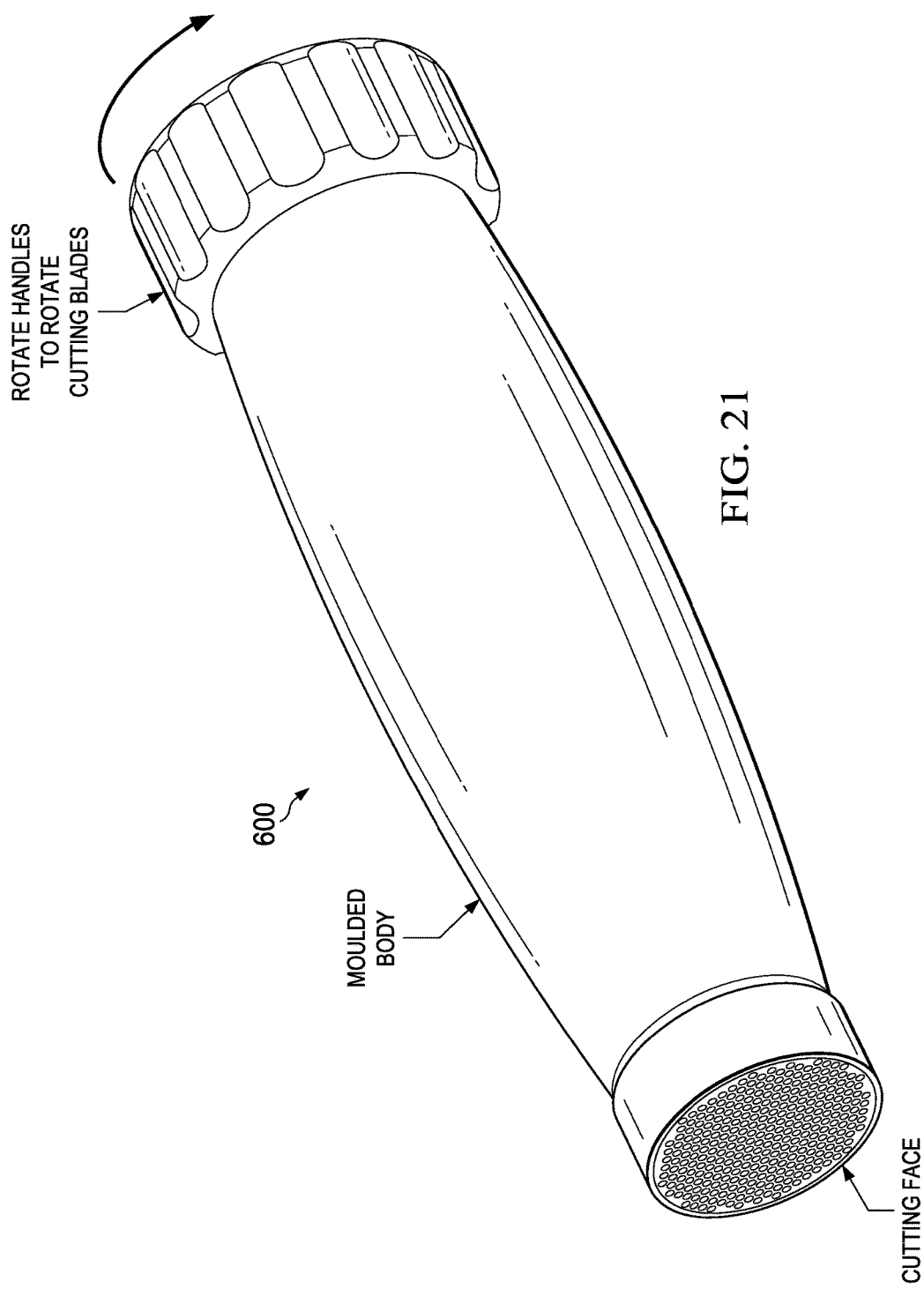
FIGS. 21-22 illustrate perspective and orthographic views of a fourth exemplary embodiment.
Figure 22:
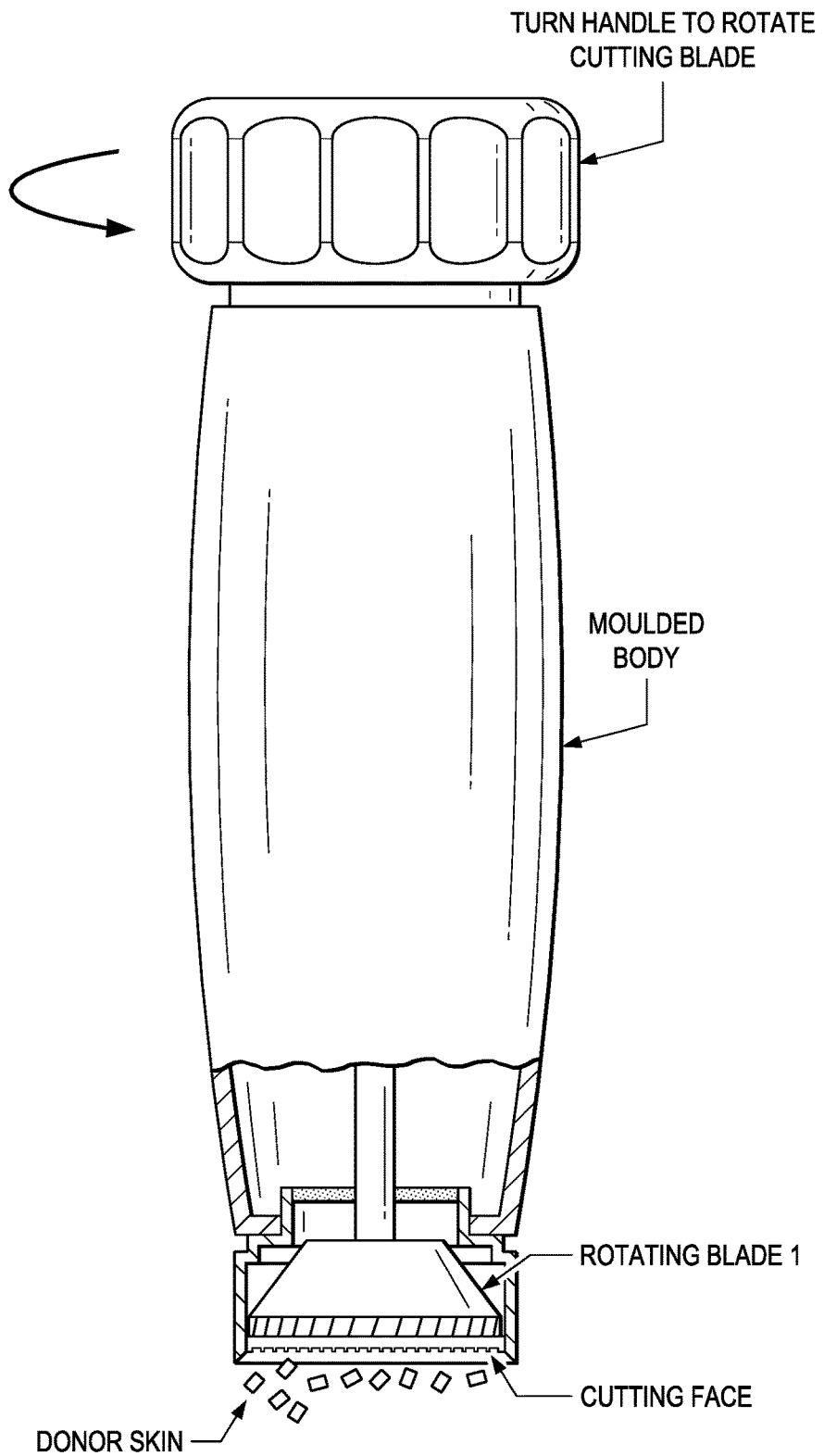

Referring now to FIGS. 21-22, a disposable, single-use skin mincer is illustrated. In this embodiment, the donor skin can be harvested using a dermatome or Weck knife and then placed into the device. Exemplary embodiments of this device comprise two contra-rotating blades which are operated by rotating the handle, which grind the donor skin tissue into small particles. The finished skin particles can be ejected from the device once the required dimensions have been achieved. This embodiment provides a unique method of processing the donor skin by using a twisting action to prepare the donor skin ready for grafting. Additional details regarding the features and operation of the embodiment of FIG. 21-22 can be found in the figures and accompanying description in FIGS. 21-22.

The claims are not intended to include, and should not be interpreted to include, means-plus- or step-plus-function limitations, unless such a limitation is explicitly recited in a given claim using the phrase(s) "means for" or "step for," respectively.

We claim:

1. A device for obtaining a plurality of skin tissue particles, the device comprising:
   a first portion having a conical end and a cylindrical end coupled to a base of the conical end and an aperture in an apex of the conical end, the first portion having a flow path through the first portion from the aperture to the cylindrical end, the aperture configured to be coupled to a low pressure source;
   a second portion having a first end configured to be coupled to the cylindrical end of the first portion to form a cavity, the second portion being cylindrical and having a second end that is closed, the second portion being separable from the first portion;
   a plurality of needles coupled to the second end of the second portion, each of the plurality of needles being hollow and in fluid communication with the aperture when the second portion is coupled to the first portion; and
   a dressing configured to be disposed in the cavity and in fluid communication with the aperture and the plurality of needles.

2. The device of claim 1, wherein each of the plurality of needles is tapered, an end of each needle proximate to the second end of the second portion being larger than a distal end.

3. The device of claim 1, further comprising a seal coupled to the second portion, the seal surrounding the plurality of needles.

4. The device of claim 1, wherein the first portion further comprises a surface extending across the cylindrical end, the surface having a plurality of apertures.

5. The device of claim 4, wherein the cavity is formed between the surface extending across the cylindrical end of the first portion and the second end of the second portion.

6. The device of claim 1, wherein the cylindrical end of the first portion has an outer diameter, the second portion has an outer diameter, and the outer diameter of the first portion is substantially the same as the outer diameter of the second portion.

7. The device of claim 6, wherein the second portion further comprises an annular tab having an outer diameter less than the outer diameter of the second portion to form an annular shoulder, the annular shoulder configured to receive the cylindrical end of the first portion.

* * * * *